US008391580B2

(12) United States Patent
Bornfleth (10) Patent No.: US 8,391,580 B2
(45) Date of Patent: Mar. 5, 2013

(54) IMAGE PROCESSING
(75) Inventor: Harald Bornfleth, Fuerstenfeldbruck (DE)
(73) Assignee: DePuy Orthopaedie GmbH (DE)
(*) Notice: Subject to any disclaimer, the term of this patent is extended or adjusted under 35 U.S.C. 154(b) by 32 days.
(21) Appl. No.: 12/671,662
(22) PCT Filed: Jul. 30, 2008
(86) PCT No.: PCT/IB2008/002569
§ 371 (c)(1), (2), (4) Date: Jun. 29, 2011
(87) PCT Pub. No.: WO2009/016509
PCT Pub. Date: Feb. 5, 2009

(65) Prior Publication Data
US 2011/0249882 A1 Oct. 13, 2011

(30) Foreign Application Priority Data
Aug. 1, 2007 (GB) ..................................... 0714940

(51) Int. Cl.
*G06K 9/00* (2006.01)
(52) U.S. Cl. ........................................ 382/132; 382/128
(58) Field of Classification Search .................. 382/100, 382/107, 128–134, 154, 275, 289–295; 600/1–9, 600/407, 410, 425, 476, 595; 128/922; 348/77, 348/8, E07.085; 356/455–456; 378/4, 22, 378/62, 15–20, 95, 98, 98.11
See application file for complete search history.

(56) References Cited

U.S. PATENT DOCUMENTS
6,683,972 B1* 1/2004 Mathiak ........................ 382/131
7,184,814 B2* 2/2007 Lang et al. .................... 600/416
7,889,906 B2* 2/2011 Smith et al. ................... 382/132

2003/0083596 A1* 5/2003 Kramer et al. ................ 600/595
(Continued)

FOREIGN PATENT DOCUMENTS
GB 2416101 A 1/2006
WO WO 2005107597 A1 11/2005

OTHER PUBLICATIONS
PCT International Search Report and Written Opinion PCT/IB2008/002569, dated Apr. 21, 2009.
UK Search Report GB0714940A dated Nov. 8, 2007.
Beyar R et al: "Prospective Motion Correction of X-Ray Images for Coronary Interventions" IEEE Transactions on Medical Imaging, Apr. 1, 2005, pp. 441-450 vol. 24, No. 4, IEEE Service Center, Piscataway, NJ, US, XP011129442, ISSN: 0278-0062.

*Primary Examiner* — Matthew Bella
*Assistant Examiner* — Mehdi Rashidian (57) ABSTRACT

A method and image processing system for correcting motion artefacts in captured projection images of a body part caused by movement relative to the co-ordinate system of an imaging system between capture of the images are described. A first image data set is obtained representing a first captured image of the body part for which the imaging system had a first geometry. A second image data set is obtained representing a second captured image of the same body part for which the imaging system had a second geometry and in which the second captured image is from a different direction to the first captured image. The position of at least a first anatomical landmark point is identified in the first captured image from first image data set. The position of the at least first anatomical landmark point is projected into the second captured image. A transformation required to map the position of the same anatomical landmark point from the second image data set onto the projected position of the at least first anatomical landmark is determined. The so determined transformation represents the true position of the body part relative to the imaging system when the second image was captured.

10 Claims, 3 Drawing Sheets

U.S. PATENT DOCUMENTS

| | | |
|---|---|---|
| 2004/0015072 A1 | 1/2004 | Pelletier et al. |
| 2005/0220264 A1* | 10/2005 | Homegger ........................ 378/8 |
| 2006/0133564 A1 | 6/2006 | Langan et al. |
| 2008/0015433 A1* | 1/2008 | Alexander et al. ............ 600/427 |
| 2008/0221442 A1* | 9/2008 | Tolkowsky et al. ........... 600/425 |
| 2009/0052760 A1* | 2/2009 | Smith et al. ................... 382/132 |
| 2010/0157041 A1* | 6/2010 | Klaiman et al. ................ 348/77 |

* cited by examiner

IMAGE PROCESSING

CROSS REFERENCE TO RELATED APPLICATION

The present application is a continuation of International Patent Application No. PCT/IB2008/002569 filed Jul. 30, 2008.

The present invention relates to image processing, and in particular to methods and apparatus for processing images to compensate for any movement of a subject between images.

BACKGROUND OF THE INVENTION (1) Field of the Invention.

Various imaging technologies, whether analogue or digital, are widely used in medical applications to capture images of internal structures of a body and particularly bones. In some applications, it can be useful to capture multiple images of a body part. In some applications, it does not matter if the body part moves between image captures. However, in other applications it can be important that the body part remains stationary between image captures. For example, in applications in which images of the same body part from different directions are required, it can be important that there is no movement of the body part between image captures, otherwise, it can be difficult to determine whether a feature in the image is a genuine feature of the body part or an artefact created by movement of the body part between image captures.

For example, multiple X-ray images of the same body part can be used to instantiate a statistical shape model of the body part. If there is movement of the body part between X-ray image captures, then the instantiated model may be less accurate, as it is trying to fit to an artefact in the image data set, rather than to the pure image data.

Fiducials with a known geometry can be used so that the position of the body part relative to the fiducials can be determined from captured images including the fiducials. However, in the time that passes between the acquisition of two projection images, the subject may move with respect to the fiducials that are to be used to register the image into one coordinate system. This may occur when imaging soft tissues, e.g. the heart, or when imaging extremities like legs or arms, if the fiducials are not rigidly attached to the object of interest. For example, in pre-operative bone model calculation, the calibration object can sometimes not be attached rigidly to the body part (especially in obese patients, or for the pelvis, the femur, humerus, etc.).

In the case of movement of a rigid body part, e.g. a bone, and few images, the motion artefact may not easily be recognized, and an incorrect reconstruction of the imaging system geometry may occur.

(2) Description of Related Art

US Patent application publication number US 2005/0220264 A1 describes a technique in which projection images are corrected to nullify any motion. However, image correction often results in errors due to interpolation artefacts.

Hence, it would be advantageous to be able to reduce the existence of artefacts in image data resulting from movement of a body part between image captures.

BRIEF SUMMARY OF THE INVENTION

According to a first aspect of the invention, there is provided a method for correcting motion artefacts in captured images of a body part of a subject caused by movement of the body part between capture of the images by the imaging system. A first image data set is provided which represents a first captured image of the body part for which the imaging system had a first geometry. A second image data set is provided representing a second captured image of the same body part for which the imaging system had a second geometry. The second captured image is from a different direction to the first captured image. The position of at least a first anatomical landmark point is identified in the first captured image using the first image data set. The position of the first anatomical landmark point is projected into the second captured image. Back-projection information from the first landmark can be used. A transformation required to map the position of the same anatomical landmark point from the second image data set onto the projected position of the first anatomical landmark is determined. The so determined transformation represents or can be used to obtain the true position of the body part relative to the imaging system when the second image was captured.

Hence, the present invention is based on the approach of correcting the imaging geometry according to the changes in position of the body part detectable in the captured images. This leaves the images unchanged and hence does not introduce artefacts as can occur in approaches based on correcting the images themselves.

Back projecting a position from the first image into three-dimensional (3-D) space results in a series of positions in 3-D space along the back projection ray. Projecting these positions onto the second image results in a line in the second image. The projected position can correspond to a line of the second image. A maximum and a minimum value can define the length of the line.

The method can further comprise determining the separation between the projected position, or line, for the first anatomical landmark point and the position of the same anatomical landmark in the second image. The separation can be determined by the perpendicular separation between the projection line and the position of the same landmark in the second image.

Determining the transformation can include minimising the separation. The separation can be expressed as a normalised value, and preferably normalised to unity.

Various minimisation algorithms can be used, such as the Simplex algorithm.

A plurality of different anatomical landmark points can be used. For example, at least three different anatomical landmark points for a given body part can be used.

Projecting the position of the at least first anatomical landmark point can comprise transforming the position of the first anatomical landmark point in the first image into the 3D co-ordinate system of the imaging system. Projecting the position can further comprise transforming from the 3D co-ordinate system of the imaging system into positions in the second image. Preferably, transformation matrices are used.

Determining the transformation can include applying a parameterised transformation. The parameters can be varied during minimisation. The transformation can be applied using a transformation matrix.

Angular rotations and/or translations can be parameterised. Preferably, three rotation angles and three translations are parameterised.

The method can further comprise using the positions in the captured images of orthonormal incidence of the imaging system to determine the positions of the anatomical landmark in the first and second images.

The method can be applied to images captured by various types of imaging systems. The imaging system can be an X-ray imaging system, and preferably a digital X-ray imaging system. Such systems are particularly suitable for imaging bones, in which case the body part being imaged can include at least one bone.

Preferably, the body part that was imaged includes at least a part, or the whole, of at least one joint of the subject's body. The body part can be a knee joint, ankle joint, hip joint, shoulder joint, spinal joint and similar.

The method can further comprise instantiating a statistical shape model, using the first image data set, the second image data set and the transformation.

The method can further comprise capturing the first image and the second image.

A further aspect of the invention provides computer program code executable by a data processing device to carry out the method aspect of the invention. A further aspect of the invention is a computer readable medium bearing such computer program code.

A further aspect of the invention provides an image processing system for correcting motion artefacts in captured images of a body part of a subject caused by movement of the body part relative to the co-ordinate system of an imaging system between capture of the images by the imaging system. The image processing system can include at least a first storage device storing a first image data set representing a first captured image of the body part for which the imaging system had a first geometry and a second image data set representing a second captured image of the same body part for which the imaging system had a second geometry in which the second captured image is from a different direction to the first captured image. A controller can also be provided which is configured to, or is capable of, identifying the position of at least a first anatomical landmark point in the first captured image from the first image data set, projecting the position of the at least first anatomical landmark point into the second captured image and determining a transformation required to map the position of the same anatomical landmark point from the second image data set onto the projected position of the first anatomical landmark. The so determined transformation represents or can be used to obtain the true position of the body part relative to the imaging system when the second image was captured.

BRIEF DESCRIPTION OF THE DRAWINGS

An embodiment of the invention will now be described, by way of example only, and with reference to the accompanying drawings, in which.

Similar items in different Figures share common reference numerals unless indicated otherwise.

DETAILED DESCRIPTION OF THE INVENTION

Generally, the method of the invention uses features of projection images of bones that are taken from different angles. Bone landmarks in the projection images are identified. For a known imaging geometry, the position of a landmark identified in one projection image, translates into a trajectory in each of the other projection images. Herein, "imaging geometry" means the relative position of the source of the projection image with respect to the image plate for each of the projection images.

If the same landmarks are identified in the second, and any further, images, then the method determines if the same landmarks lie on the trajectories that would be predicted by the imaging geometry. If not, then the imaging geometry was wrongly estimated. This can happen if a calibration object containing fiducials is not rigidly attached to the object of interest (e.g. a bone). Or, more generally, because the bone has moved with respect to the calibration object between two acquisitions.

The invention is interested in the spatial relationship between two, or more, images of the same bone, taken from different angles. If the bone moved with respect to the calibration object, then the transformation that describes this movement should be introduced into the imaging geometry. The parameters of the transformation are varied until the correct transformation is found (i.e. the transformation that results in landmarks of the second image being as close as possible to the trajectories calculated from landmarks of the first image). Hence, the correct transformation is related to how the bone must have moved in order for the two images to be of the same bone captured from different directions. The transformation can then be used in other applications that require the two images to be available in a common frame of reference, e.g. for instantiating a statistical shape model.

The method of the invention differs from photogrammetric approaches in that the projection image shows not points on a surface, but a projection through the structure. It therefore leaves fewer structures with a clear correspondence in three-dimensional space between the images.

The method also differs from alignment procedures using Fourier transform methods. Those methods rely on the assumption that the imaging geometry is similar between the images (e.g. an orthogonal projection geometry). However, the centre beam of the cone beam projection will not necessarily be part of the image.

Having described the method of the invention at high-level, a more detailed description will now be provided with reference to the Figures.

Figure 1:
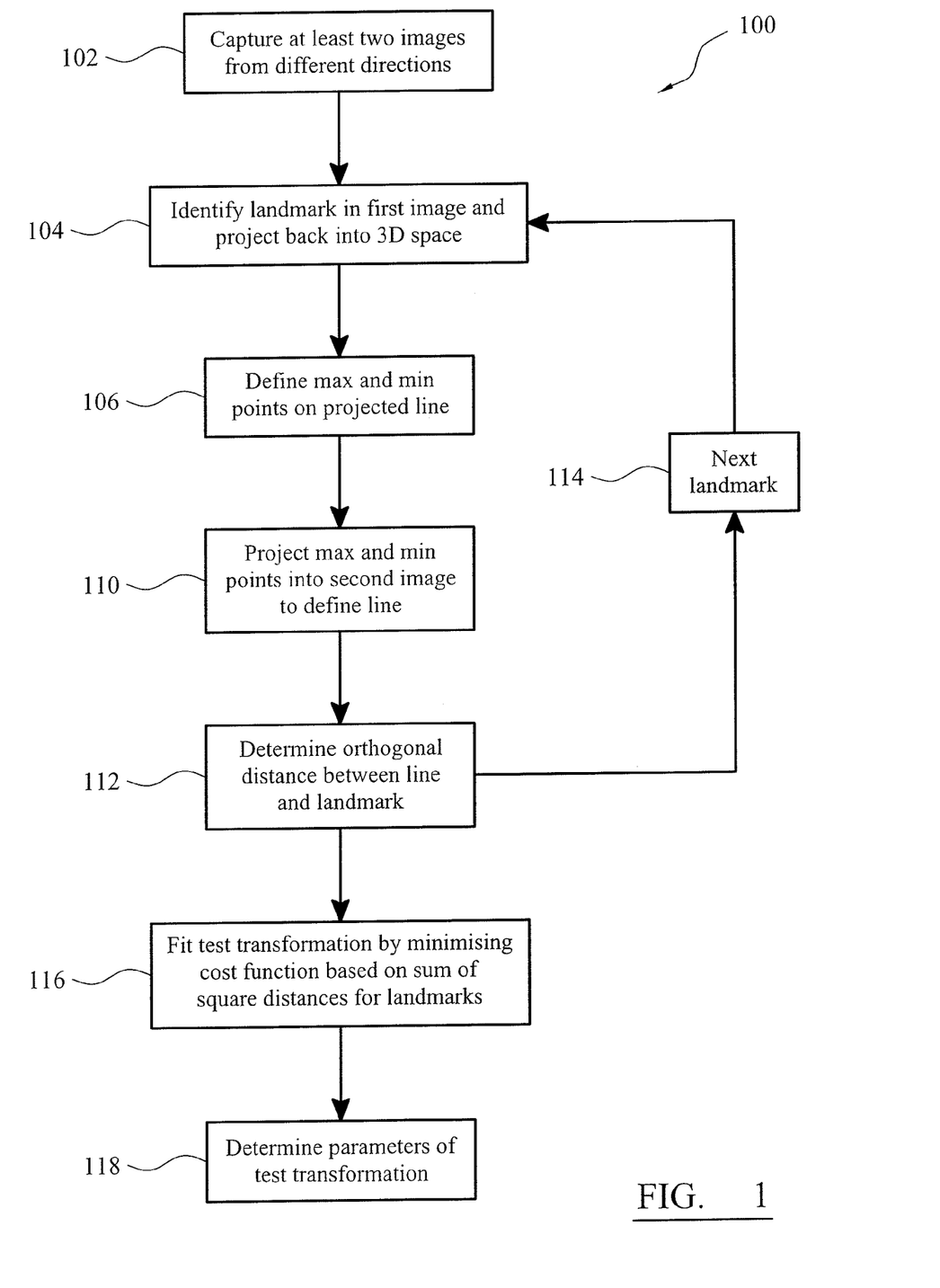
FIG. 1 shows a flow chart illustrating an image correction method of the invention.

FIG. 1 shows a flow chart illustrating the image correction method 100 of the invention. Pre-operatively, either immediately or some time before surgery, at least two images of the patient's body part are captured 102 from different directions by an imaging system. By capturing at least two images from different directions of the same body part, three dimensional structural information about the body part can be obtained.

Figure 2:
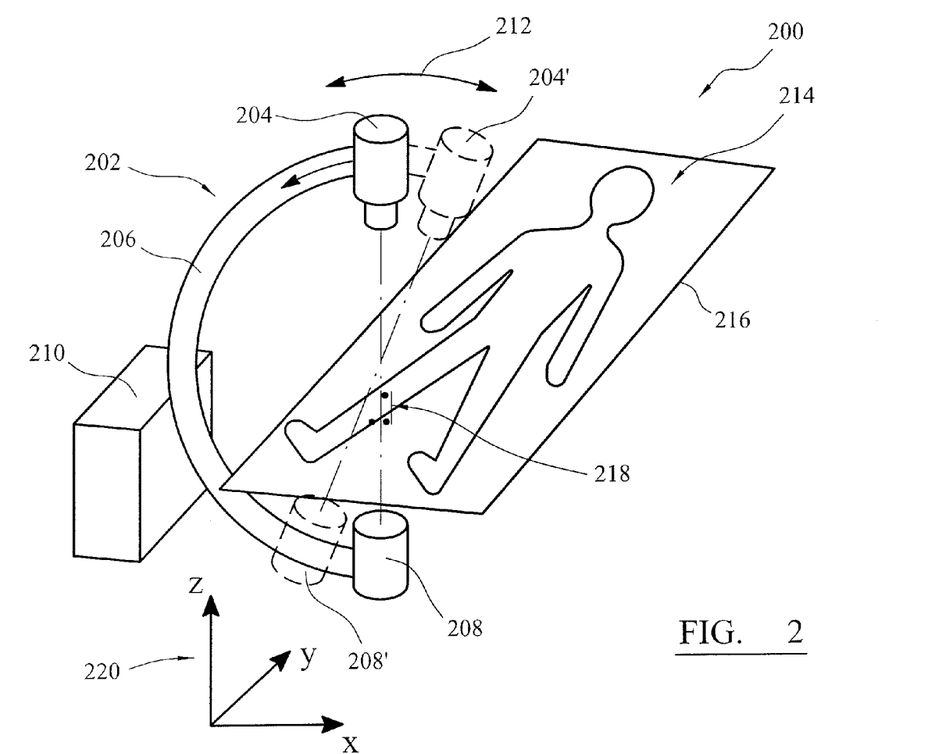
FIG. 2 shows a schematic perspective view of an X-ray imaging system capturing first and second images of a body part of a patient.

FIG. 2 shows a schematic diagram illustrating a system 200 used to carry out the image capture step 102. An imaging system 202, in the form of a digital X-ray imaging system 202, includes an X-ray source 204 attached at a first end of a C-arm 206 and a digital X-ray image detector 208 at a second end of the C-arm. In other embodiments, an analogue X-ray system can be used, and then the images from the X-ray films are digitised for processing. The C-arm is mounted on a housing 210 containing various electronics for controlling image capture and moving the C-arm about a circle as illustrated by double headed arrow 212.

A patient 214 lies on a support surface 216, positioned so that the X-ray beam passes through the part of the patient being imaged, in the illustrated example, the patient's knee joint. An X-ray calibration phantom 218 is also located on the support surface adjacent the patient's knee so that the calibration phantom is also present in the captured images. X-ray calibration phantoms are generally known in the art and include a number of X-ray opaque fiducial markers having a known spatial arrangement, in terms of their relative positions and separations. The position of the X-ray source which captured an image including the fiducials of the phantom can be determined using geometry based on the appearance of the fiducials in the captured image in a manner generally understood in the art.

As illustrated in FIG. 2, a first X-ray image is captured with the X-ray source 204 and X-ray detector 208 in a first position, and then at least a second X-ray image is captured with the X-ray source 204' and X-ray detector 208' in a second position (as illustrated by dashed lines in FIG. 2). Images from at least two different directions of the bone are captured, but the accuracy and reliability of the method can be improved by capturing images from more than two different directions. The arbitrary co-ordinate frame 220 for the imaging system is illustrated in FIG. 2. As can be seen, the C-arm pivots about the y-axis and two dimensional X-ray images are captured generally in the x-y plane.

Figure 3:
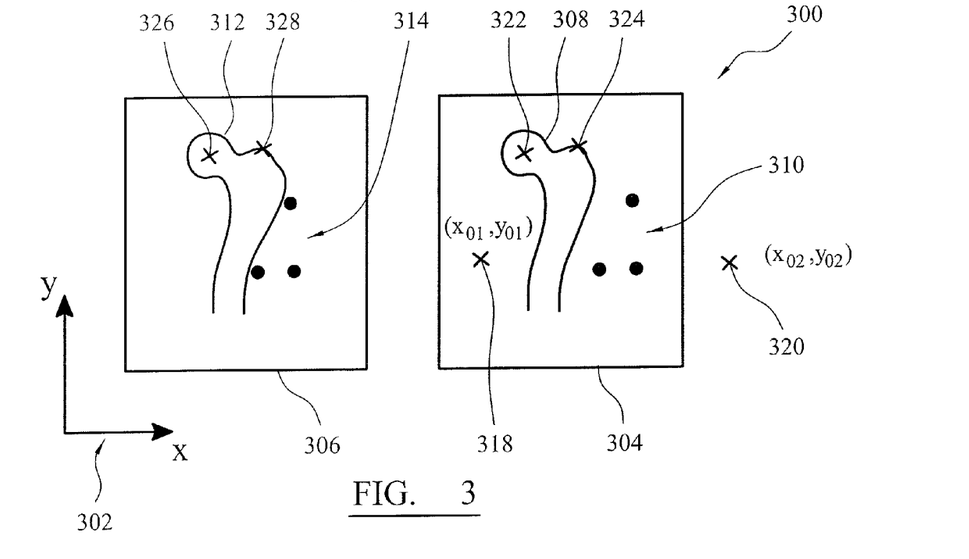
FIG. 3 shows a graphical representation of X-ray images of the same body part captured from different directions.

FIG. 3 illustrates the of two radiographs 300 of the femoral head of a patient captured by the imaging system projected into the x-y plane 302. The first radiograph 304 was captured with the X-ray source in the first position and the second radiograph 306 was captured with the X-ray source in the second position. The first radiograph includes a first projection image of the femoral head 308 of the patient and the fiducials 310 of the calibration phantom 218. The second radiograph includes a second projection image of the femoral head 312 of the patient and the fiducials 314 of the calibration phantom 218. The point 318 marks the point in the x-y plane where the X-ray beam has orthogonal incidence on the imaging plane for the first image, and has co-ordinates $(x_{o1}, y_{o1})$. The point 320 marks the point in the x-y plane where the X-ray beam has orthogonal incidence on the imaging plane for the second image, and has co-ordinates $(x_{o2}, y_{o2})$, and may not actually fall in the captured image, as illustrated in FIG. 3. Also shown in FIG. 3 are the positions of first and second anatomical landmark points 322 and 324, e.g. the centre of the femoral head and the tip of the greater trochanter, in the first image 304, and the positions of the same two anatomical landmark points 326, 328 in the second image 306.

FIG. 3 illustrates the scenario in which there has been no movement of the patient's body part between capture of the first and second images. The image plane does not rotate as the X-ray source is rotated about the y-axis. Rather the image plane simply translates in the x-y plane. From the positions of the fiducials 310, 314 in the images and the positions of the orthogonal points of incidence 318, 320 it is possible to back project for each image into the 3-D co-ordinate system to determine the position that the X-ray source must have been at in order to generate the image of the fiducials present in the captured image. If there has been no movement of the bone in the reference frame 220 between images, then any differences in the images of the bone must be due solely to the differences in the imaging geometry and the actual shape of the bone. Therefore, as the different imaging geometries can be determined from the fiducials, it is possible to use both images simultaneously to instantiate a 3-D statistical shape model of the bone for an accurate reconstruction of the 3-D shape of the bone.

As illustrated in FIG. 3, the position of the bone image 308 in the image 304 and the position of the bone image 312 in the image 306 is generally the same. That is there has been no shift in the position of the bone image between image captures. This means that certain movements of the bone have not occurred. However, if the bone has only translated in the x-direction between image captures, then it would not be possible to distinguish this movement of the bone within the images from the movement of the images themselves owing to rotation of the C-arm about the y-axis, which generally causes a translation of the imaging planes in the x-direction.

Figure 4A:
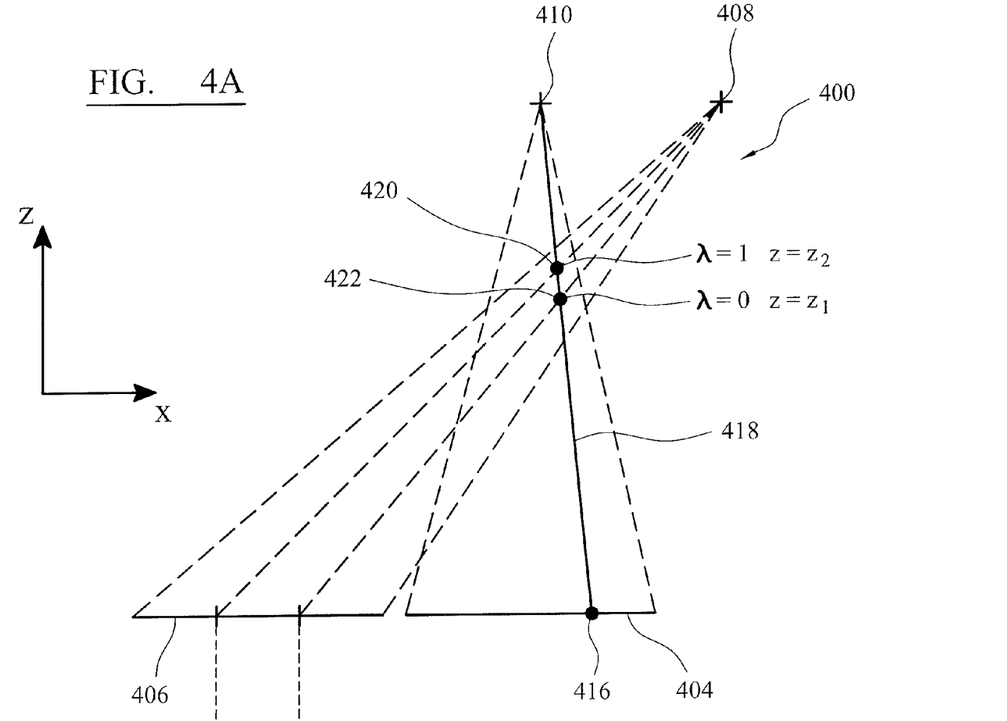
FIG. 4A shows a graphical representation of the imaging geometry during capture of the two images and illustrating part of the method of FIG. 1.
Figure 4B:
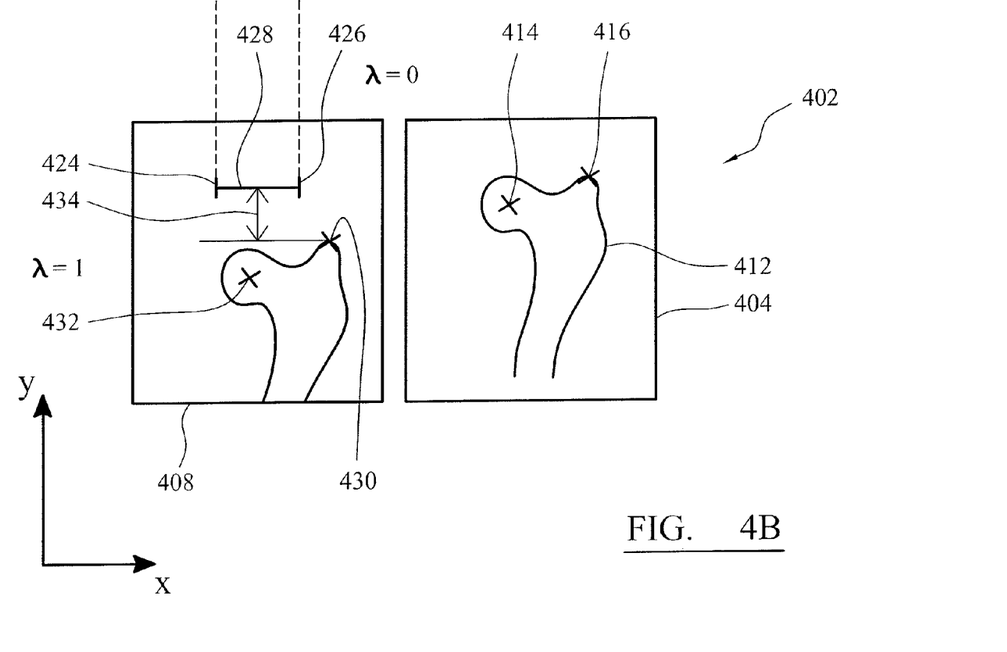
FIG. 4B shows a graphical representation of the X-ray images of FIG. 4B.

FIG. 4A shows a graphical representation of the imaging geometry 400 in the z-x plane, and FIG. 4B shows corresponding captured first and second projected images 402 in the y-x plane, similar to those of FIG. 3, but omitting the fiducial points in the images and the positions of orthogonal incidence. The first image 404 was captured with the X-ray source in a first position 410 and the second image 406 with the x-ray source in a second position 408. Image 404 includes an image of the femur of the patient 412, and includes two anatomical landmarks, the centre of the femoral head 414 and the tip of the greater trochanter 416. At step 104, the position of a number of anatomical landmarks in the captured bone image are identified, e.g. points 414 and 416.

In the following formulae, vectors include a leading unit element in order to facilitate the notation of matrix transformations for combined rotations and translations, i.e. using the homogeneous coordinate approach.

The position of the ith landmark on image 1 is:

$$r_1^i = \begin{pmatrix} 1 \\ x_1^i \\ y_1^i \end{pmatrix}$$

and the position of the ith landmark on image 2 is:

$$r_2^i = \begin{pmatrix} 1 \\ x_2^i \\ y_2^i \end{pmatrix}$$

The landmark point 416 in the image is projected back into 3D space to the position 410 of the X-ray source at step 104, as illustrated by line 418. The position of the X-ray source, 408, can be determined from the images of the fiducial points in the image 406, as described above. In practice, the point 416 in the first image is transformed into a common 3D co-ordinate system using the matrix:

$$T_{1-3D}(\lambda) = \begin{pmatrix} 1 & 0 & 0 \\ x_{o,1}\left(1 - \frac{z_1 - \lambda(z_2 - z_1)}{z_0}\right) & \frac{z_1 - \lambda(z_2 - z_1)}{z_0} & 0 \\ y_{o,1}\left(1 - \frac{z_1 - \lambda(z_2 - z_1)}{z_0}\right) & 0 & \frac{z_1 - \lambda(z_2 - z_1)}{z_0} \\ z_1 - \lambda(z_2 - z_1) & 0 & 0 \end{pmatrix}$$

where $$\lambda \in [0,1]$$

and encodes the position on the ray 418 from the point in the image to the x-ray source position. The x-ray source 410 is considered to lie at point z=0 on the z axis. The position of the image plane 404 on the z axis, is denoted $z_o$, and $z_1$ and $z_2$ are the heights enclosing the image volume of interest, as shown in FIG. 4A, with $z_o > z_1 > z_2$. At step 106, maximum 420 and minimum 422 positions in 3D space along the line 418 are defined by setting λ to 0 and 1.

Then at step 110 the maximum 420 and minimum positions 422 in 3D space are projected into the second image 406, and the points 424, 426 in the second image corresponding to the maximum and minimum positions define a line 428 in the second image. In practice, the maximum and minimum positions 420, 422 can be projected into the second image using the matrix:

$$T_{3D-2}(\lambda) = \begin{pmatrix} 1 & 0 & 0 & 0 \\ x_{o,2}\left(1 - \dfrac{z_0}{z_1 - \lambda(z_2 - z_1)}\right) & \dfrac{z_0}{z_1 - \lambda(z_2 - z_1)} & 0 & 0 \\ y_{o,2}\left(1 - \dfrac{z_0}{z_1 - \lambda(z_2 - z_1)}\right) & 0 & \dfrac{z_0}{z_1 - \lambda(z_2 - z_1)} & 0 \end{pmatrix}$$

In the second image 406, points 430 and 432 correspond to the same anatomical landmarks 414,416. At step 112 the orthogonal distance 434 between the projected line 428 and the landmark is determined. The length of the orthogonal line 434 is normalised to length 1 for entering in a formula below. In this way, the scalar product of the normalised line with the vector pointing from the landmark to any point on the projected line yields the orthogonal distance. The normalised orthogonal line is referred to as "ortholine" in the formula below. As illustrated by return line 114, the above process is generally carried out for all n anatomical landmarks identified in the images at step 104.

Then at step 116, a transformation $T_{3D1 \to 3D2}$ between the 3-D positions of bony landmarks for the first exposure and the second exposure is found that minimises the lengths of the orthogonal lines between all n landmark points in the second image and the corresponding projected lines, e.g. the length of orthogonal line 434 between line 428 and landmark 430, i.e.

$$\sum_{i=1}^{n} (([T_{3D \to 2} T_{3D1 \to 3D2}(p) T_{1-3D}(\lambda = 0) \cdot r_1^i] - r_2^i) \cdot ortholine^i)^2 \to \min$$

where p contains the transformation parameters that can be varied $p = (d_x, d_y, d_z, \alpha, \beta, \gamma)$ (e.g. rotation angles and translations). The transformation can be parameterised as:

$$T_{3D1-3D2} = \begin{pmatrix} 1 & 0 & 0 & 0 \\ d_x & & & \\ d_y & & R(\alpha, \beta, \gamma) & \\ d_z & & & \end{pmatrix}$$

where d is a displacement vector, and R is a rotation matrix with α, β, γ the rotation angles around the x, y and z axes:

$R(\alpha\beta\gamma) =$ $$\begin{pmatrix} \cos(\gamma) & \sin(\gamma) & 0 \\ -\sin(\gamma) & \cos(\gamma) & 0 \\ 0 & 0 & 1 \end{pmatrix} \begin{pmatrix} \cos(\beta) & 0 & -\sin(\beta) \\ 0 & 1 & 0 \\ \sin(\beta) & 0 & \cos(\beta) \end{pmatrix} \begin{pmatrix} 1 & 0 & 0 \\ 0 & \cos(\alpha) & \sin(\alpha) \\ 0 & -\sin(\alpha) & \cos(\alpha) \end{pmatrix}$$

The algorithm used for minimisation can be a standard algorithm for minimization, such as the Simplex algorithm. Hence, the resulting transformation parameters for the minimisation can be determined at step 118 and specify the transformation that will map the position of the imaged body part from the first exposure to the second exposure. Hence, patient body related motion artefacts can be removed from the captured image data so that the image data more accurately represents only the shape of the body part. The transformation parameters allow the true position of the X-ray source with respect to the bone when the second image was captured to be determined.

For example, in FIG. 4B, the downward shift of the bone image in the second image 406 may be as a result of movement of the patient along the patient support in the y-direction between image captures. Using the transformation parameters, that patient motion artefact can effectively be included in the reconstruction of the imaging geometry, so that the significant differences between the bone images will reflect primarily the differences in the imaging geometry between acquisitions. The invention does not actually change the images themselves, but rather the imaging geometry reconstruction.

In general there are three rotations and three translations of the patient's body part that are possible. Assuming that the x-ray system is rotated around the y-axis before the second projection image, a translation in the x-direction cannot easily be identified as it is masked by the similar effect caused by the unknown positions of the landmarks on the back projection ray. Translations in the y-direction will shift all landmarks up or down in the second image. Translations in the z-direction will increase or decrease spacing between landmarks. Rotations about the y-axis are difficult to detect as all landmarks will stay on the same line. Rotation about the x-axis has similar effects to a translation along the z-axis, but in practice a translation along the z-axis will be a very difficult movement for a patient to make and therefore unlikely to occur. Rotation about the z-axis will result in different sized landmark position changes in the second image depending on the position of the landmark. If the x coordinate of the landmark is close to the rotation axis then not much movement will be seen in the second image. If the x-coordinate of the landmark is further away from the rotation axis, then greater amounts of movement will be seen in the second image.

Hence, displacements or rotations that happen in the same plane as the one affected by the rotation of the x-ray source will not be detected. For example, if the x-ray source rotates around the y axis, as illustrated in FIG. 1, then a bone displacement along the x axis will be difficult to detect. Similarly, a bone rotation around the y axis will be difficult to detect. This is because a displacement that can be described by these parameters will result in a displacement of landmarks in the second image along the line of the projection of landmarks in the first image, with no component of that displacement perpendicular to that line. A displacement along the z axis will be difficult to distinguish from a rotation around the x axis, but only one of those is likely to occur for a given bone structure to be imaged. Any displacement in the y axis, or rotation around x or z axes can be corrected for by this method.

In the example application of the invention described above, correction is applied to the recording of two X-rays from two different angles for creating a model of the proximal femur bone. The x-ray source is rotated around the body main axis for the second exposure. For this case, the parameters that can not be corrected are: lateral movement of the bone, vertical movement of the bone, and inward/outward rotation of the bone. The first two are unlikely to happen since the pelvis will rest firmly on the table during x-ray acquisition. Inward/outward rotation of the bone can be prevented by rotating inward before acquiring the x-ray (which is following a standard procedure), and fixing the leg in that rotation, e.g., at the feet. In this situation, a flexion of the leg or an abduction are the most likely movement artefacts, both of which can be corrected using the described method.

The number of landmarks that is needed for a successful correction depends on the application. The minimum number for correcting for the three degrees of freedom mentioned above is three landmarks. In the example of the proximal femur, these landmarks could be: (I) the centre of the femoral head; (ii) the medial portion of the tip of the greater trochanter; and (iii) the most proximal part of the lesser trochanter If the X-ray images are to be used to instantiate a statistical shape model, then the transformation parameters are obtained at step 118. The first X-ray image is compared to a digitally reconstructed radiograph from the statistical shape model. To create the second digitally reconstructed radiograph from the statistical shape model, the same motion artefact is applied during the projection, to reconstruct the actual imaging geometry as in the original X-ray capture of the second image.

The invention is not limited to use with statistical shape models and can also be used in radiostereometric analysis (RSA) type methods to correct motion artefacts.

The X-ray images do not need to be captured with the patient on a support. For example, the X-ray images can be captured with the patient kneeling or standing. Further, the X-ray images can be captured of any part of the anatomy that can be imaged by X-rays, or other imaging modalities, but is particularly suitable for bones and joints.

The accuracy of the method can be increased if more landmarks are identified. The accuracy can also be increased by identifying landmarks using an automated image processing procedure. It is important, however, that the same landmark is projected on the two projection images. For example, this is not necessarily the case for bone contours. Depending on from where a bone is imaged, a different part of the bone surface may be prominent in the projection image.

In another embodiment small implanted particles can be used that show in the projection image as bony landmarks. These particles can be automatically recognized using software that evaluates the images.

The method of the invention can be embodied in an image processing system which has access to the data sets representing the digital images captured by the X-ray system. The image processing system can be provided as part of the X-ray imaging system or as a stand alone system or as part of another system, such as part of a computer assisted surgery system. For example, the image processing system can be provided as part of a modelling system of a computer assisted surgery system and the image data and the transformation data generated by the method can be supplied to a statistical shape modelling method to generate a more accurate statistical shape model, based on the X-ray images and the true position of the bone relative to the imaging system when the images were captured. The image processing system can be implemented entirely in hardware, or as a combination of hardware and software.

It will be appreciated that in the above description of the invention, reference has been made to various features of the images, such as a line in the image. However, it will be appreciated that there is no need for such features of the images to be generated and displayed. Rather all that is required is for such features to be represented by data, e.g. mathematically, for the invention to function and so the terms in the description and claims referring to such features should be construed accordingly.

The invention claimed is:

1. A method for correcting motion artefacts in captured projection images of a bone of a subject caused by movement of the bone relative to the co-ordinate system of an imaging system between capture of the images by the imaging system, comprising the steps of:
    obtaining a first image data set representing a first captured projection image of the bone for which the imaging system had a first geometry in the co-ordinate system;
    obtaining a second image data set representing a second captured projection image of the same bone for which the imaging system had a second geometry in the co-ordinate system, and in which the second captured projection image is captured from a direction different than the direction used to capture the first captured projection image;
    identifying the position of at least a first anatomical landmark point of the bone in the first captured projection image from the first image data set;
    projecting the position of the at least first anatomical landmark point of the bone into the second captured projection image;
    determining a transformation required to map the position of the first anatomical landmark point of the bone from the second image data set onto the projected position of the at least first anatomical landmark point of the bone, wherein the so determined transformation allows the true position of the bone relative to the imaging system when the second image was captured to be determined without changing the captured projection images themselves; and
    using the positions in the captured images of orthogonal incidence of an X-ray beam of the imaging system on an imaging plane to determine the positions of the anatomical landmark in the first and second images.

2. The method of claim 1, and further comprising the step of:
    determining the separation between the projected position of the at least first anatomical landmark point and the position of the first anatomical landmark in the second image, and wherein the step of determining the transformation includes minimising the separation.

3. The method of claim 1, wherein a plurality of anatomical landmark points are used.

4. The method of claim 1, wherein the step of projecting the position of the at least first anatomical landmark point comprises transforming the position of the first anatomical landmark point in the first image into the three-dimensional co-ordinate system of the imaging system and then transforming from the three-dimensional co-ordinate system of the imaging system into positions in the second image.

5. The method of claim 2, wherein the step of determining the transformation comprises applying a parameterised transformation and the parameters are varied during minimisation.

6. The method of claim 5, wherein three rotation angles and three translations are parameterised.

7. The method of claim 1, wherein the imaging system is an X-ray imaging system.

8. The method of claim 1, and further comprising the step of:
    instantiating a statistical shape model of the bone, using the first image data set, the second image data set and the transformation.

9. A Computer program embodied as computer-executable instructions stored on a non-transitory computer-readable medium for correcting motion artefacts in captured projection images of a bone of a subject caused by movement of the bone relative to the co-ordinate system of an imaging system between capture of the images by the imaging system, the program comprising instructions for:

obtaining a first image data set representing a first captured projection image of the bone for which the imaging system had a first geometry in the co-ordinate system;

obtaining a second image data set representing a second captured projection image of the same bone for which the imaging system had a second geometry in the co-ordinate system, and in which the second captured projection image is captured from a direction different than the direction used to capture the first captured projection image;

identifying the position of at least a first anatomical landmark point of the bone in the first captured projection image from the first image data set;

projecting the position of the at least first anatomical landmark point of the bone into the second captured projection image;

determining a transformation required to map the position of the first anatomical landmark point of the bone from the second image data set onto the projected position of the at least first anatomical landmark point of the bone, wherein the so determined transformation allows the true position of the bone relative to the imaging system when the second image was captured to be determined without changing the captured projection images themselves; and using the positions in the captured images of orthogonal incidence of an X-ray beam of the imaging system on an imaging plane to determine the positions of the anatomical landmark in the first and second images.

10. A non-transitory computer readable storage medium for correcting motion artefacts in captured projection images of a bone of a subject caused by movement of the bone relative to the co-ordinate system of an imaging system between capture of the images by the imaging system, the medium having stored thereon a computer program comprising instructions, which, when executed by a computer, cause the computer to:

obtain a first image data set representing a first captured projection image of the bone for which the imaging system had a first geometry in the co-ordinate system;

obtain a second image data set representing a second captured projection image of the same bone for which the imaging system had a second geometry in the co-ordinate system, and in which the second captured projection image is captured from a direction different than the direction used to capture the first captured projection image;

identify the position of at least a first anatomical landmark point of the bone in the first captured projection image from the first image data set;

project the position of the at least first anatomical landmark point of the bone into the second captured projection image;

determine a transformation required to map the position of the first anatomical landmark point of the bone from the second image data set onto the projected position of the at least first anatomical landmark point of the bone, wherein the so determined transformation allows the true position of the bone relative to the imaging system when the second image was captured to be determined without changing the captured projection images themselves; and use the positions in the captured images of orthogonal incidence of an X-ray beam of the imaging system on an imaging plane to determine the positions of the anatomical landmark in the first and second images.

* * * * *